United States Patent [19]

Conroy et al.

[11] Patent Number: 6,001,253

[45] Date of Patent: Dec. 14, 1999

[54] LIQUID CHROMATOGRAPHY COLUMN

[75] Inventors: Christine M. Conroy, Charlottesville, Va.; Jeffrey R. Green, San Francisco, Calif.; Jeffrey A. Kaster; Peter J. Leavesley, both of Charlottesville, Va.; Thomas C. Ransohoff, Lexington, Mass.

[73] Assignee: Dyax Corporation, Cambridge, Mass.

[21] Appl. No.: 09/291,893

[22] Filed: Apr. 14, 1999

Related U.S. Application Data

[62] Division of application No. 08/984,138, Nov. 26, 1997, which is a continuation of application No. 08/649,429, May 16, 1995, abandoned.

[51] Int. Cl.$^6$ ............................................. B01D 15/08
[52] U.S. Cl. ................................. 210/635; 210/656
[58] Field of Search ............................. 210/635, 656, 210/659, 198.2, 232, 238, 282; 96/101, 106; 530/413, 417

[56] References Cited

U.S. PATENT DOCUMENTS

| | | | |
|---|---|---|---|
| 2,998,036 | 8/1961 | Strasheim et al. | 141/72 |
| 3,300,849 | 1/1967 | Wiseman | 29/124 |
| 3,398,512 | 8/1968 | Perkins, Jr. et al. | 55/386 |
| 3,440,864 | 4/1969 | Blume | 73/61.1 |
| 3,511,377 | 5/1970 | Hrdina | 210/198 |
| 3,615,235 | 10/1971 | Hrdina | 25/253 |
| 3,935,884 | 2/1976 | Hazelton | 141/80 |
| 3,966,609 | 6/1976 | Godbille et al. | 210/198 |
| 4,250,035 | 2/1981 | McDonald et al. | 210/198.2 |
| 4,280,905 | 7/1981 | Gunkel et al. | 210/198.2 |
| 4,361,482 | 11/1982 | Teetz et al. | 210/198.2 |
| 4,375,743 | 3/1983 | Sullivan | 53/470 |
| 4,384,957 | 5/1983 | Crowder, III et al. | 210/656 |
| 4,451,365 | 5/1984 | Sattler et al. | 210/198.2 |
| 4,483,374 | 11/1984 | Siemion | 141/9 |
| 4,549,584 | 10/1985 | Morin et al. | 141/73 |
| 4,557,830 | 12/1985 | Onitsuka | 210/198.2 |
| 4,565,632 | 1/1986 | Hatch et al. | 210/656 |
| 4,582,608 | 4/1986 | Ritacco | 210/656 |

(List continued on next page.)

OTHER PUBLICATIONS

Snyder, Introduction to Modern Liquid Chromatography, John Wiley & Sons, New York, 1979, pp. 624–625.

BioSepro, "HyperDiffusion Chromatography", pp. 6, 7, 13, Apr. 1995.

Pharmacia Biotech—Process Products '95, "High Purity in Industrial Chromatography" pp. 1–5 undated.

POROS 50 EP and OH Perfusion Chromatography, "Operating Instructions" pp. 1 and 2 undated.

3M Emphaze—Biosuport Medium, "Introduction to 3M Emphaze Biosupport Medium", 1992, pp. 1–3.

EM Separations Technology, "Tentacle Ion Exchange Chromatography Handbook", pp. 1 and 4 undated.

Biotage (Separations at Any Scale), "Lighting Fast Flash Chromatography Cartridges" 1995, pp. 1 and 2.

EM Separations Technology—Superformance Pilot and Production Glass Columns, "Chromatography Columns" pp. 68–71, 1995.

Toyopearl®, "Affinity Chromatography", pp. 1 and 2 undated.

Skea, "Process High Performance Liquid Chromatography", High Performance Liquid Chromatography, vol. 98, pp. 489–500. undated.

*Primary Examiner*—Ernest G. Therkorn
*Attorney, Agent, or Firm*—Fish & Richardson P.C.

[57] ABSTRACT

A chromatography cartridge assembly includes a cartridge with a flexible wall defining a chamber, and a porous, polymeric, hydrophilic, chromatography media contained within the chamber. The chromatography media has an operating pressure rating greater than 3 bars. The flexible wall forms a movable diaphragm for compressing the chromatography media. The chromatography cartridge assembly includes a flow distributor, flow collector, and sieves formed from a hydrophilic material. A compression module defines a pressure chamber for containing a pressurized fluid. The pressurized fluid acts to move the flexible wall of the cartridge assembly. The compression module has a pressure ratings greater than 3 bars.

8 Claims, 4 Drawing Sheets

U.S. PATENT DOCUMENTS

| | | | |
|---|---|---|---|
| 4,597,866 | 7/1986 | Couillard | 210/198.2 |
| 4,627,918 | 12/1986 | Saxena | 210/656 |
| 4,636,315 | 1/1987 | Allen, Jr. | 210/656 |
| 4,636,316 | 1/1987 | Harris et al. | 210/198.2 |
| 4,670,141 | 6/1987 | Shackelford et al. | 210/198.2 |
| 4,732,687 | 3/1988 | Muller | 210/198.2 |
| 4,737,292 | 4/1988 | Ritacco et al. | 210/656 |
| 4,755,293 | 7/1988 | Sakamoto | 210/198.2 |
| 4,769,141 | 9/1988 | Couillard | 210/198.2 |
| 4,865,728 | 9/1989 | Larsson | 210/198.2 |
| 4,882,047 | 11/1989 | Shalon | 210/198.2 |
| 4,890,753 | 1/1990 | Duryee et al. | 53/527 |
| 4,891,133 | 1/1990 | Colvin, Jr. | 210/198.2 |
| 4,927,531 | 5/1990 | Sakamoto et al. | 210/198.2 |
| 4,968,421 | 11/1990 | Spacek | 210/198.2 |
| 5,021,162 | 6/1991 | Sakamoto et al. | 210/635 |
| 5,069,069 | 12/1991 | Miyagishi | 73/335 |
| 5,137,628 | 8/1992 | Hart | 210/198.2 |
| 5,141,635 | 8/1992 | Leplang | 210/198.2 |
| 5,167,810 | 12/1992 | Vassarotti | 210/198.2 |
| 5,192,433 | 3/1993 | Shalon | 210/198.2 |
| 5,238,556 | 8/1993 | Shirkhan | 210/198.2 |
| 5,282,973 | 2/1994 | Mann | 210/198.2 |
| 5,324,426 | 6/1994 | Joseph | 210/198.2 |
| 5,338,448 | 8/1994 | Gjerde | 210/198.2 |
| 5,378,361 | 1/1995 | Baeckstrum | 210/198.2 |
| 5,423,982 | 6/1995 | Jungbauer | 210/198.2 |
| 5,482,628 | 1/1996 | Schick | 210/198.2 |
| 5,601,708 | 2/1997 | Leavesley | 210/198.2 |
| 5,671,928 | 9/1997 | Lanyi et al. | 277/207.2 |
| 5,714,074 | 2/1998 | Karllson et al. | 210/656 |
| 5,714,677 | 2/1998 | Parsy et al. | 96/105 | ns.

LIQUID CHROMATOGRAPHY COLUMN

This application is a division of U.S. application Ser. No. 08/984,138, filed Nov. 26, 1997, which, in turn, is a continuation of application Ser. No. 08/649,429, filed May 16, 1995, now abandoned.

BACKGROUND OF THE INVENTION

This invention relates to liquid chromatography columns useful in biomolecule separations.

Matrix materials used in liquid chromatography for separations of biomolecules must be hydrophilic to prevent denaturation of the biomolecule leading to precipitation and non-specific adsorption on the matrix material. Standard matrix materials used for bioseparations have been soft gels such as sepharose® with pressure ratings up to 3 bars. This limits the pressure that can be applied to the process fluid, thus limiting the speed of separation. Matrix materials have conventionally been packed in glass or stainless steel housings.

Advances in materials technology have led to the development of a new class of polymeric, hydrophilic and rigid support matrices that have much higher pressure ratings and can achieve better resolution. These materials include Emphaze™, POROS®, HyperD™, Fractogel®, and Sources™.

SUMMARY OF THE INVENTION

The invention features, in general, a chromatography cartridge assembly including a cartridge with a flexible wall defining a chamber, and a polymeric, hydrophilic, chromatography media contained within the chamber. The chromatography media has an operating pressure rating greater than 3 bars. The flexible wall forms a movable diaphragm for compressing the chromatography media.

In preferred embodiments, the media has a particle size in the range of about 15–200 microns. The chromatography media is selected from the group consisting of Emphaze™, POROS®, HyperD™, Source™, Toyopearl®, and Fractogel® media. The chromatography cartridge assembly includes a flow distributor, flow collector, and sieves formed from a hydrophilic material. There are seals located between the flow distributor and an inner surface of the flexible wall and between the flow collector and an inner surface of the flexible wall. The seal is an o-ring or is formed by welding the flow distributor and flow collector to the inner surface. The movable diaphragm radially compresses the chromatography media. The cartridge has a diameter of at least about 3 inches.

According to another aspect of the invention, a chromatography apparatus includes a compression module surrounding the cartridge assembly. The compression module defines a pressure chamber for containing a pressurized fluid. The pressurized fluid acts to move the flexible wall of the cartridge assembly.

In preferred embodiments, the chromatography apparatus includes first and second end caps for securing the chromatography cartridge assembly within the compression module. The end caps define passages for flow of process fluid. A flow distributor includes an inlet aligned with the passage of the first end cap. The flow distributor inlet and the passage of the first end cap define a process fluid inlet channel. The first end cap has a seal located between the first end cap and the flow distributor for preventing leakage of process fluid from the inlet channel. A flow collector includes an outlet aligned with the passage of the second end cap. The flow collector outlet and the passage of the second end cap define a process fluid outlet channel. The second end cap has a seal located between the second end cap and the flow collector for preventing leakage of process fluid from the outlet channel. The seals keep the compression module free of process fluid contamination during use. A pressure source is connected to the compression module. The compression module has a pressure rating greater than 3 bars, and preferably greater than 10 to 15 bars.

According to another aspect of the invention, a chromatography cartridge assembly includes a flexible walled cartridge defining a chamber for containing chromatography media; a flow distributor for distributing process fluid across a cross-sectional area of the chamber; a flow collector for collecting process fluid from across a cross-sectional area of the chamber; and two sieves, one on either end of the chamber, for retaining the chromatography media in the chamber. The sieves prevent passage of the media while permitting passage of the process fluid. The flow distributor, flow collector, and sieves are formed of hydrophilic material.

In preferred embodiments, the hydrophilic materials have a surface energy greater than about 36 dyn/cm.

According to another aspect of the invention, a chromatography method includes providing a chromatography cartridge assembly, applying compression to the chromatography media, and supplying a pressurized biomolecule sample in an aqueous based solvent.

In preferred embodiments, the sample is supplied at a pressure greater than 3 bars. The compression is applied to the chromatography media in a radial direction and is greater than or equal to the pressure of the sample.

According to another aspect of the invention, a method of revitalizing a packed column having trapped air includes applying compression, e.g., in a radial direction, to chromatography media to minimize the volume of trapped air.

Advantages include liquid chromatography of biomolecule process fluids under pressures above 3 bars. The materials used in the chromatography apparatus prevent biomolecule precipitation and non-specific adsorption. The cartridge within a module system permits changeout of wetted components and reuse of the module for different biomolecules without cross-contamination.

Other advantages and features of the invention will ba apparent from the following description of a preferred embodiment thereof and from the claims.

BRIEF DESCRIPTION OF THE DRAWINGS

The drawings will be described first.
Drawings
FIG. 2A is a top view of the pressure module of FIG. 2;
FIG. 2B is an enlarged view of the clamping region of the pressure module of FIG. 2.

DESCRIPTION OF THE PREFERRED EMBODIMENT

Figure 1:
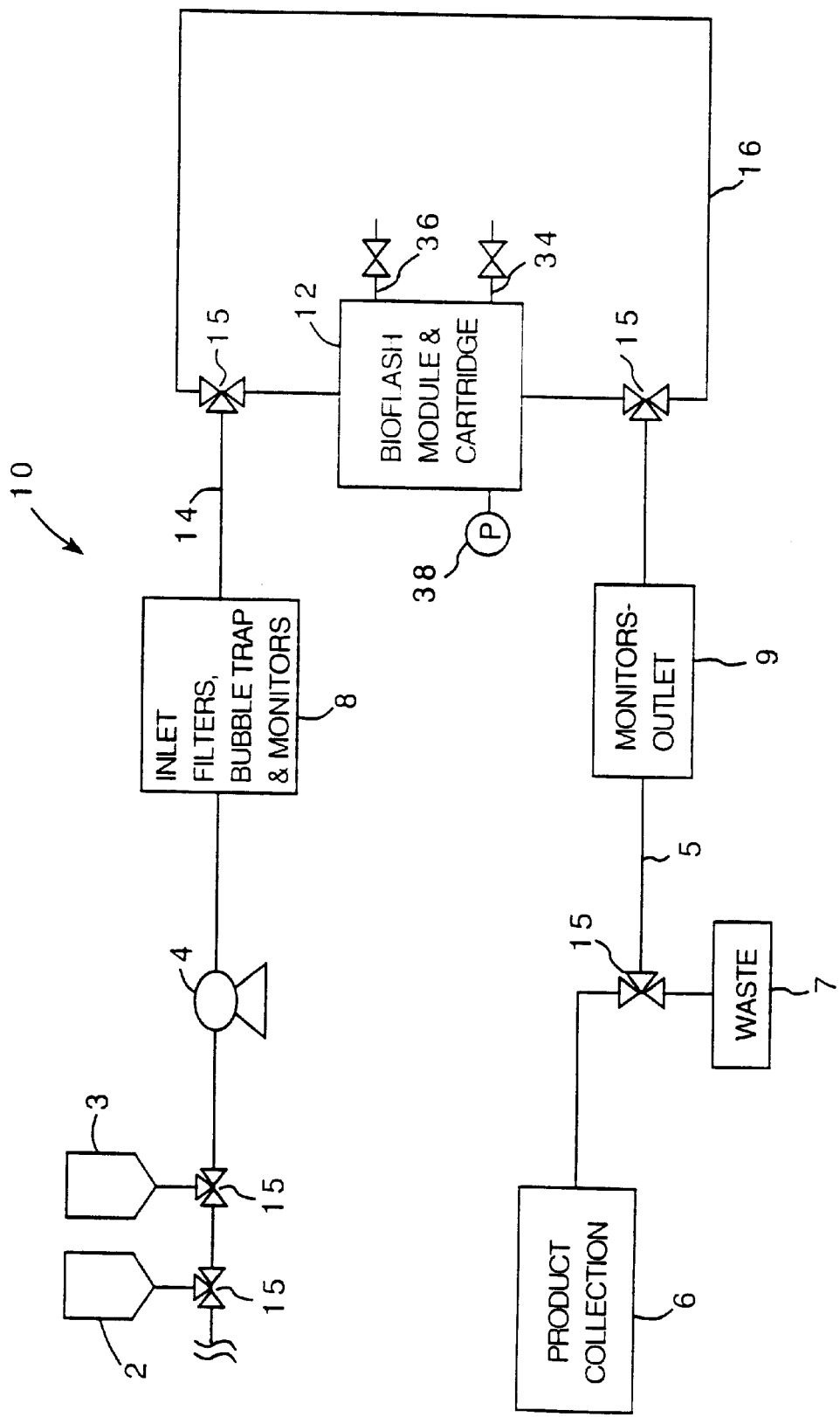
FIG. 1 is a schematic of a chromatography apparatus according to the invention.

Referring to FIG. 1, an apparatus 10 is shown for performing chromatography separation of biomolecules, e.g., proteins, oligosaccharides, large DNA molecules, and viral particles, in an aqueous based solvent. The term biomolecules is not meant to include synthetic organic chemicals, small linear peptides, or chiral compounds. Apparatus 10 includes a chromatography assembly 12 and inlet solution tank 2, load tank 3, and system pump 4 for delivering process fluid under pressure along a process inlet path 14 to chromatography assembly 12. An outlet line 5 leads from chromatography assembly 12 to a product collection vessel 6 and a waste receptacle 7. A water filter, bubble trap and monitor 8 (monitoring, e.g., pressure, conductivity, and pH) are located along the process fluid inlet path 14. A monitor 9 monitoring, e.g., pressure, conductivity, pH, and UV absorbance, is located along outlet line 5. A column bypass 16 permits the system to be cleaned while bypassing the chromatography assembly. Valves 15 control the flow of the process fluid.

Figure 2:
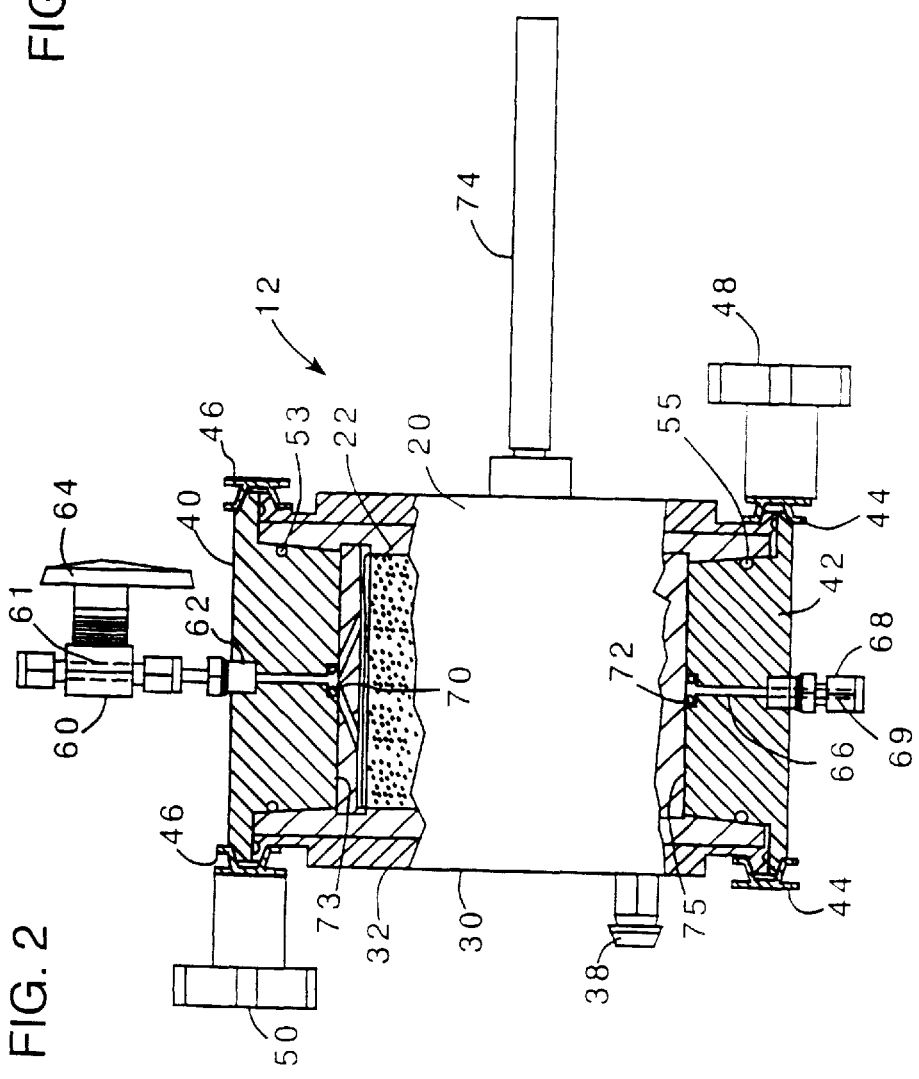
FIG. 2 is a partially cut-away, cross-sectional side view of the pressure module of the invention.

Referring to FIGS. 2–2B, chromatography assembly 12 includes a compression module 20 and a cartridge assembly 22. Compression module 20 includes a housing 30, formed from, e.g., stainless steel or aluminum, defining a cylindrical region 32 for containing fluid for applying radial compression to cartridge assembly 22. A compressible or incompressible fluid can be used to apply radial compression pressure to cartridge assembly 22.

The application of radial compression to a chromatography cartridge is described in U.S. Pat. No. 4,250,035 to McDonald, hereby incorporated by reference. Briefly, in a liquid chromatography column, a stationary phase such as silica is packed in a cartridge having a flexible wall. By exerting radial pressure on the cartridge, packing bed voids are avoided and wall channeling effects are overcome. The packing efficiency of the column is increased and is more reproducible, and greater uniformity can be achieved in column performance both among packed columns of the same kind and during the useful life of a given packed column.

Referring to FIGS. 1 and 2A, housing 30 includes a fluid inlet 34, a relief valve 36 for purging pressure within cylindrical region 32, and a pressure indicator 38. Radial compression pressure applied to cartridge assembly 22 is controlled by a pressure regulator or a pump (not shown) which delivers fluid to fluid inlet 34; solvent flow rate through the cartridge assembly is controlled by pump 4. A mounting arm 74 connected to housing 30 can be used to mount chromatography assembly 12 to a laboratory stand.

Removable end caps 40, 42 retain cartridge assembly 22 in place within compression module 20. Referring particularly to FIG. 2B, end cap 42 is mounted to housing 30 with a band clamp 44 (end cap 40 is similarly mounted to housing 30 with a band clamp 46). Clamp tightening knobs 48, 50 are used to tighten band clamps 44, 46 respectively. At higher pressures, the knobs can be replaced with bolts to meet code requirements. As shown in FIG. 2B, each end cap 40, 42 is sealed against housing 30 with an o-ring 52 to prevent leakage of compression fluid from region 32. As shown in FIG. 2, end caps 40, 42 are sealed against cartridge assembly 22 by o-rings 53, 55, respectively, which separate compression fluid from process fluid.

An inlet connector 60 defines a channel 61 leading to an inlet passage 62 defined by end cap 40 for flow of process fluid into cartridge assembly 22. Control knob 64 is used to open and close channel 61. An outlet passage 66 defined by end cap 42 leads to an outlet connector 68 defining a channel 69 for flow of process fluid out of cartridge assembly 22. Inlet and outlet passages 62 and 66 include o-ring seals 70, 72, respectively, for sealing the passages against cartridge assembly 22. End caps 40, 42 are preferably made from a hydrophilic material, e.g., stainless steel, to prevent precipitation of biomolecules on the surfaces of passages 62, 66. Seals 70 and 72 prevent flow of process fluid along the interface 73 between end cap 40 and cartridge 22 and the interface 75 between end cap 42 and cartridge 22 thus minimizing the exposure of the process fluid to dead spaces and crevices in which microbial growth and attachment could occur.

Figure 3:
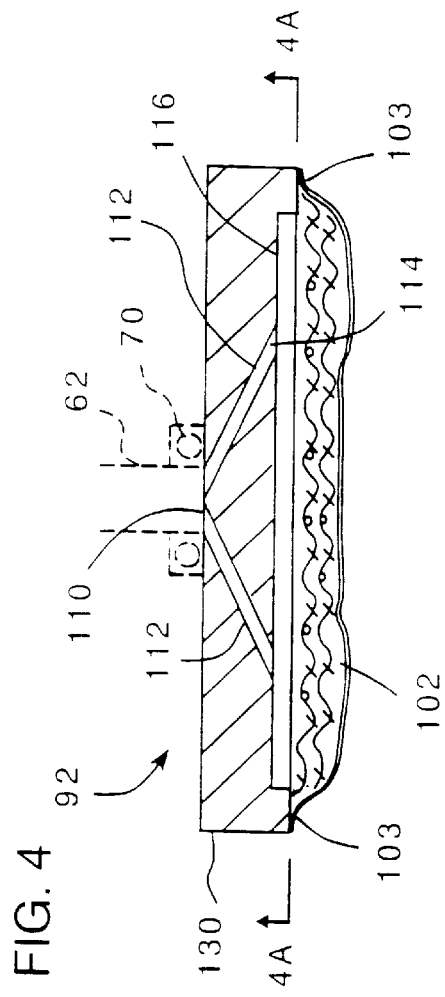
FIG. 3 is a partially cut-away, cross-sectional side view of a cartridge assembly of the invention.

Referring to FIG. 3, cartridge assembly 22 has a flexible wall 80 partially defining a media chamber 82. Flexible wall 80 further defines end cap receiving openings 84, 86. The upper and lower ends 88, 90 of media chamber 82 are defined by flow assemblies 92, 94 respectively. Upper flow assembly 92 includes a flow distributor 100 and a sieve 102, e.g., a mesh or frit. A mesh is preferred over a frit due to its smaller surface area which limits biomolecule adhesion. Lower flow assembly 94 includes a flow collector 104 and a sieve 106. The flow distributor 100, flow collector 104, and sieves 102, 106 are preferably made from hydrophilic materials having surface energies greater than about 36 dyn/cm, e.g., polyamide, polyethyleneterephthalate, polyvinylidene chloride, polymethylmethacrylate, and polystyrene, to limit biomolecule binding to the surfaces and clogging of the sieves.

Figure 4:
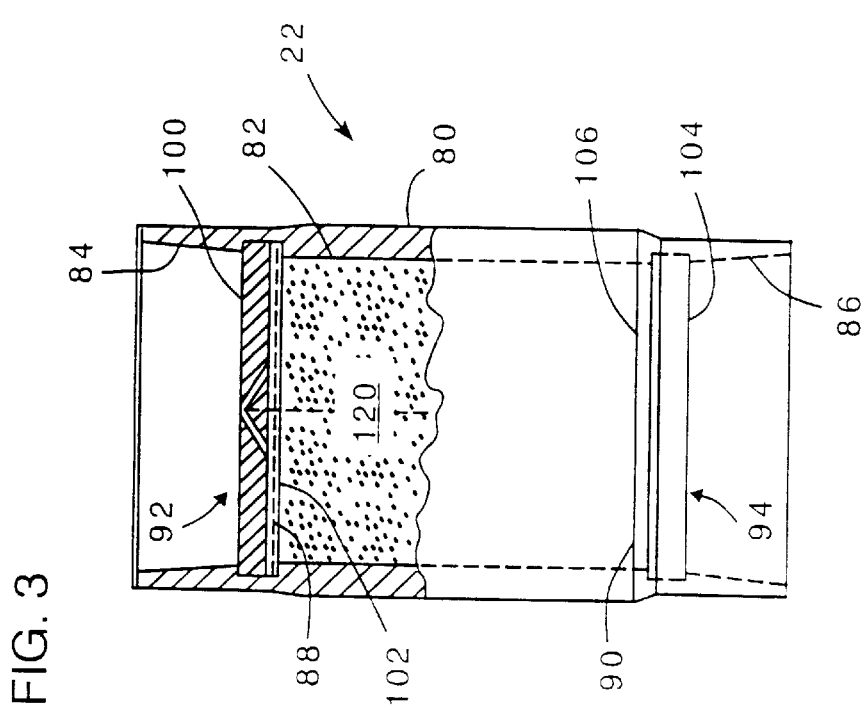
FIG. 4 is a cross-sectional side view of a distributor and mesh of the invention.
Figure 4A:
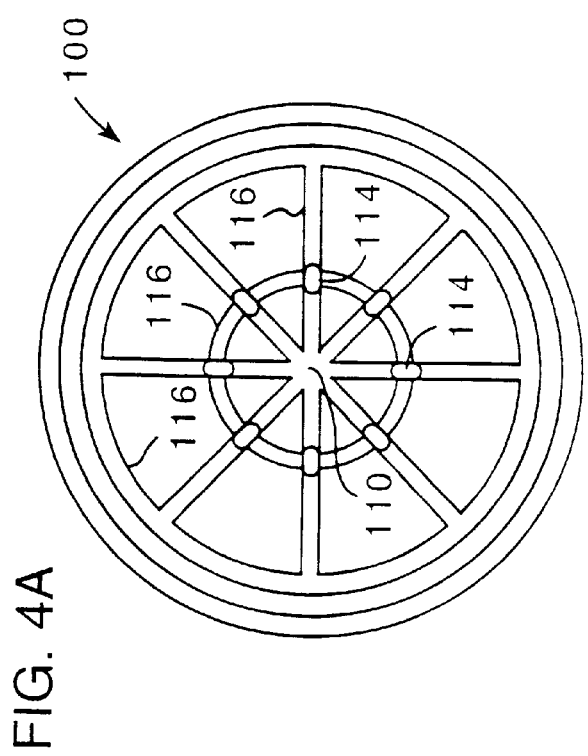
FIG. 4A is a sectional view of the distributor of FIG. 4, taken along lines 4A—4A.

Referring to FIGS. 4 and 4a, sieve 102 is welded to flow distributor 100 along outer periphery 103 of flow distributor 100. Welding along periphery 103 permits process fluid to flow through sieve 102 but not around it, and prevents media particles from leaking around sieve 102 into flow distributor 100. Sieve 106 is similarly welded to flow collector 104.

The process fluid path is from inlet passage 62 to an inlet 110 of flow distributor 100. Multiple flow channels 112, 8 channels being shown in the illustrated embodiment, run from inlet 110 to outlets 114. Outlets 114 connect flow channels 112 to a network of channels 116 which distribute the process fluid. Sieve 102 preferably has a pore size of about 10–20 micron to allow passage of process fluid while preventing passage of chromatography media. Flow collector 104 and sieve 106 are identical to flow distributor 100 and sieve 102. Flow collector 104 and sieve 106 are mounted such that process fluid first passes through sieve 106 and then through the network of channels 116 to finally be collected at inlet 110.

Figure 5:
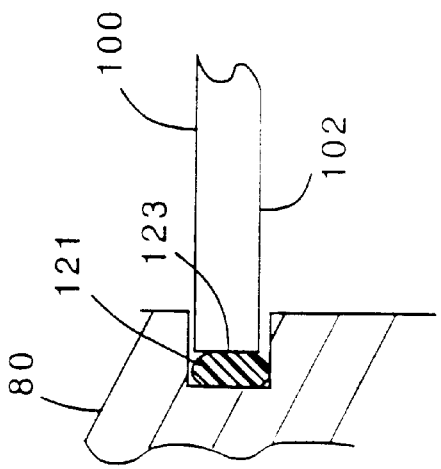
FIG. 5 is an enlarged schematic view of a sealing scheme of the invention.
Figure 6:
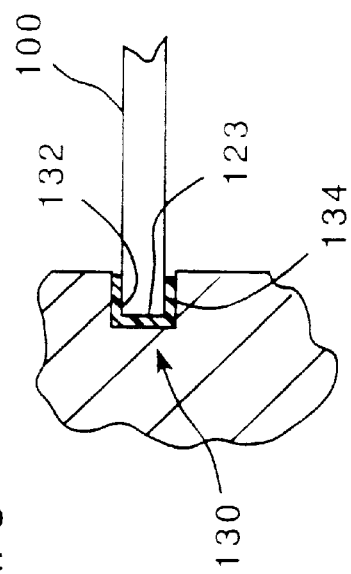
FIG. 6 is an enlarged schematic view of an additional sealing scheme of the invention.

An alternative or additional sealing scheme which further limits voids and dead spaces in which process fluid can be trapped is shown in FIG. 5. Here, an o-ring 121 positioned between flow distributor 100 and cartridge wall 80 prevents flow of process fluid around edge 123 of the flow distributor and into crevices where the process fluid can be trapped. Similarly, an o-ring can be positioned between flow collector 104 and cartridge wall 80. Additionally, referring to FIG. 6, the flow distributor and/or flow collector can be welded at 130 along edge 123 and side portions 132, 134 to the cartridge wall, thereby creating a low dead volume seal.

Example operating pressure (process fluid flow pressure) ratings achievable with chromatography assembly 12 employing an aluminum compression module 20 are listed below. For an incompressible compression fluid, the operating pressure can be equal to the pressure rating of the pressure module. For a compressible compression fluid, the operating pressure is about 1 to 6 bars less than the pressure rating of the pressure module because the compression pressure applied to the cartridge is greater than the process fluid pressure to maintain the integrity of the cartridge. Higher pressure ratings are achievable depending upon tube thickness and by substituting stainless steel for aluminum.

| inner diameter of compression module 20 (mm) | pressure (bar) |
|---|---|
| 75 | 20–35 |
| 100 | 14–23 |
| 150 | 10–17 |
| 300 | 6–14 |
| 400 | 4–10 |

Referring again to FIG. 3, chromatography media 120 is contained within media chamber 82 by upper and lower sieves 102, 106. Due to recent advances in materials technology leading to the development of the new hydrophilic and rigid support matrices having high pressure ratings, the high pressure ratings achievable with chromatography assembly 12 and the hydrophilic materials used in the critical components of cartridge assembly 22 enable fast, high resolution biomolecule separation. Suitable matrices for chromatography media 120 include Emphaze™, available from Pierce; POROS®, available from PerSeptive Biosystems; HyperD™, available from BioSepra; Source™, available from Pharmacia Biotech, Sweden; Toyopearl® available from TosoHaas, and Fractogel®, available from E.Merck, Germany. The media listed above have particle sizes in the range of 15–100 microns, though media can be used having larger particle sizes, up to at least about 200 microns. The pressure ratings and available functionalities of each material are listed below.

| Matrix | Pressure Rating (bar) | Available Functionalities |
|---|---|---|
| POROS ® | 100 | ion exchange hydrophobic interaction affinity |
| HyperD ™ | 200 | ion exchange affinity |
| Emphaze ™ | 7 | affinity |
| Fractogel ® | 10 | ion exchange hydrophobic interaction affinity |
| Toyopearl ® | at least 7 | ion exchange hydrophobic interaction affinity |
| Source ™ | 50 | ion exchange hydrophobic interaction |

All media have pressure ratings above 3 bars, above 5 bars, and some have pressure ratings about 50 bars, with one having a rating greater than 150 bars.

The radial pressure applied to the chromatography media should be at least equal to the flow pressure of the process fluid to maintain the integrity of the column. When using a compressible compression fluid, the radial pressure applied is in the range of about 1 to 6 bars over the operating pressure.

The surfaces of chromatography assembly 12 exposed to process fluid include cartridge 22, flow distributor 100, flow collector 104, sieves 102, 106, and end caps 40, 42. As discussed previously, the flow distributor, flow collector and sieves are formed from hydrophilic materials to prevent biomolecule precipitation and non-specific adsorption. The sieves are preferably polymeric as opposed to stainless steel due to the stainless steel's poorer chemical resistance and susceptibility to chloride attack. Because the surface area of cartridge 22 exposed to the process fluid is much less than that of the flow distributor, flow collector, and sieves, cartridge 22 can be formed from a less hydrophilic material, e.g., polyethylene having a surface energy of 35.7 dyn/cm (linear PE) and 35.3 dyn/cm (branched PE). Though to minimize biomolecule precipitation and non-specific adsorption on the cartridge, preferably a more hydrophilic material is also used for cartridge 22. End caps 40, 42 are preferably stainless steel.

Seals 53, 55, 70, 72 insure that compression module 20 remains free of contamination from process fluid during use. The components of cartridge assembly 12 with wetted surfaces can be changed while the same compression module 20 can be used with a new sample without cross-contamination.

It is understood that separate inserts can be employed to define passages 62, 66 such that end caps 40, 42 are not exposed to process fluid and only the inserts need be removed and exchanged or cleaned between sample runs.

It has been found that radial compression can revitalize a packed column. Trapped air in the media causes bed cracking and loss of chromatographic efficiency. By subjecting the column to radial compression, the volume of air is minimized thus minimizing the effects of air entrapment such that there is little or no decrease in performance of the column.

Other embodiments of the invention are within the scope of the following claims.

What is claimed is:

1. A method of performing chromatography separation of biomolecules in an aqueous based solvent, comprising:
   providing a chromatography cartridge assembly including
      a cartridge containing a porous, polymeric, hydrophilic chromatography media for separating biomolecules,
      an inlet flow assembly, and
      an outlet flow assembly,
   selecting the material from which the inlet flow assembly is formed from polymeric hydrophilic materials having a surface energy greater than about 36 dyn/cm to limit biomolecule binding to the inlet flow assembly, and
   passing biomolecules in aqueous based solvent through the chromatography cartridge assembly.

2. The method of claim 1 wherein the providing step includes providing an inlet flow assembly comprising a flow distributor and a sieve.

3. The method of claim 1 further comprising selecting the material from which the outlet flow assembly is formed from polymeric hydrophilic materials having a surface energy greater than about 36 dyn/cm to limit biomolecule binding to the outlet flow assembly.

4. The method of claim 3 wherein the providing step includes providing an outlet flow assembly comprising a flow collector and a sieve.

5. The method of claim 1 wherein the providing step includes providing a cartridge containing chromatography media having an operating pressure rating greater than about 3 bars.

6. The method of claim 1 wherein the providing step includes providing a cartridge containing chromatography media having a particle size in the range of about 15–200 microns.

7. The method of claim 1 wherein the providing step includes providing a cartridge having a flexible wall.

8. The method of claim 1 further comprising radially compressing the chromatography media.

* * * * *